United States Patent
Hiyama et al.

(10) Patent No.: US 7,829,730 B2
(45) Date of Patent: Nov. 9, 2010

(54) PROCESS FOR PRODUCTION OF METHYLENE DISULFONATE COMPOUND

(75) Inventors: Takehiro Hiyama, Hyogo (JP); Takeshi Takeuchi, Hyogo (JP); Hidehiko Myoken, Hyogo (JP); Hirokazu Kagano, Hyogo (JP)

(73) Assignee: Sumitomo Seika Chemicals Co., Ltd., Kako-gun, Hyogo (JP)

( * ) Notice: Subject to any disclaimer, the term of this patent is extended or adjusted under 35 U.S.C. 154(b) by 150 days.

(21) Appl. No.: 12/297,276

(22) PCT Filed: Apr. 4, 2007

(86) PCT No.: PCT/JP2007/057599

§ 371 (c)(1),
(2), (4) Date: Oct. 15, 2008

(87) PCT Pub. No.: WO2007/125736

PCT Pub. Date: Nov. 8, 2007

(65) Prior Publication Data

US 2009/0137820 A1    May 28, 2009

(30) Foreign Application Priority Data

Apr. 26, 2006    (JP)    .............................. 2006-122525

(51) Int. Cl.
C07D 549/11    (2006.01)
C07D 341/00    (2006.01)

(52) U.S. Cl. .......................................... 549/11; 549/19

(58) Field of Classification Search ................... 549/11, 549/19
See application file for complete search history.

(56) References Cited

U.S. PATENT DOCUMENTS 4,329,478 A    5/1982    Behr
4,950,768 A    8/1990    Cronyn

FOREIGN PATENT DOCUMENTS

| JP | 57-150654 A | 9/1982 |
| JP | 61-501089 A | 5/1986 |
| JP | 2005-336155 A | 12/2005 |
| JP | 2006-188449 A | 7/2006 |

OTHER PUBLICATIONS

Hcaplus 2005:1282975, "Preparation of disulfonic acid cyclic diesters", Higo et. al., 2005.*
International Search Report of PCT/JP2007/057599, date of mailing Jun. 19, 2007.

* cited by examiner

*Primary Examiner*—Janet L Andres
*Assistant Examiner*—Binta M Robinson
(74) *Attorney, Agent, or Firm*—Westerman, Hattori, Daniels & Adrian, LLP

(57) ABSTRACT

The present invention provides a process for producing a methylene disulfonate compound in a simple manner at low cost.

The present invention provides a process for producing a methylene disulfonate compound represented by General Formula (2) comprising:
reacting, in the presence of a dehydrating agent, a formaldehyde compound with a sulfonic acid compound represented by General Formula (1):

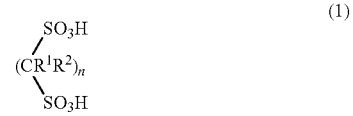

(1)

wherein $R^1$ and $R^2$ are independently a hydrogen atom or a $C_{1-4}$ alkyl group whose hydrogen atom may be substituted with halogen atom; n is an integer from 1 to 4; and when n is an integer from 2 to 4, n $R^1$s and n $R^2$s may be the same or different:

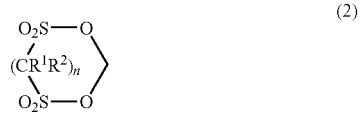

(2)

wherein, $R^1$, $R^2$, and n are the same as those described above for General Formula (1).

3 Claims, No Drawings

PROCESS FOR PRODUCTION OF METHYLENE DISULFONATE COMPOUND

TECHNICAL FIELD

The present invention relates to a process for the production of a methylene disulfonate compound.

BACKGROUND ART

Methylene disulfonate compounds are usable as pharmaceutical preparations for treating leukemia in animals, etc. Known methods for producing a methylene disulfonate compound include the following.

(1) A method wherein sulfonyl chloride is reacted with silver carbonate, and the resulting silver sulfonate is reacted with diiodomethane (WO85/03075);

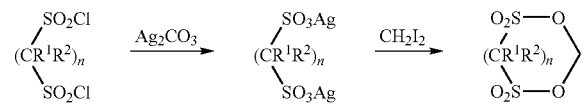

(2) A method wherein alkanedisulfonic acid is reacted with methylene diacetate (JP 2005-336155 A).

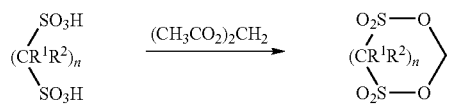

However, these methods have various drawbacks. For example, the silver carbonate and diiodomethane used in the method of (1) are expensive and the reaction is slow. The method of (2) uses methylene diacetate, which is not easily obtainable and expensive.

DISCLOSURE OF THE INVENTION

Problem to be Solved by the Invention

An object of the present invention is to provide a method by which a methylene disulfonate compound can be industrially produced in a simple manner at low cost.

Means for Solving the Problem

The present invention provides a process for the production of a methylene disulfonate compound as below.

1. A process for producing a methylene disulfonate compound represented by General Formula (2) comprising:

reacting, in the presence of a dehydrating agent, a formaldehyde compound with a sulfonic acid compound represented by General Formula (1):

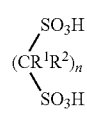 (1)

wherein $R^1$ and $R^2$ are independently a hydrogen atom or a $C_{1-4}$ alkyl group whose hydrogen atom may be substituted with halogen atom; n is an integer from 1 to 4; and when n is an integer from 2 to 4, n $R^1$s and n $R^2$s may be the same or different:

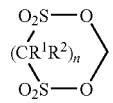 (2)

wherein, $R^1$, $R^2$, and n are the same as those described above for General Formula (1).

2. The process according to Item 1, wherein the formaldehyde compound is at least one member selected from the group consisting of paraformaldehyde, anhydrous formaldehyde and trioxane.

3. The process according to Item 1 or 2, wherein the dehydrating agent is phosphorus pentoxide.

The present invention is explained in detail below.

The sulfonic acid compound used in the present invention is a compound represented by General Formula (1) below.

 (1)

In General Formula (1), $R^1$ and $R^2$ are independently a hydrogen atom or a $C_{1-4}$ alkyl group whose hydrogen atom may be substituted with halogen atom; and n is an integer from 1 to 4.

When n is an integer from 2 to 4, n $R^1$s and n $R^2$s may be the same or different.

Examples of the $C_{1-4}$ alkyl group wherein a hydrogen atom may be substituted with a halogen atom include a methyl group, ethyl group, n-propyl group, iso-propyl group, n-butyl group, iso-butyl group, sec-butyl group, tert-butyl group, chloromethyl group, bromomethyl group, fluoromethyl group, and trifluoromethyl group.

Preferable examples of $R^1$ and $R^2$ include a hydrogen atom, methyl group, ethyl group, and n-propyl group.

Examples of the sulfonic acid compounds represented by General Formula (1) include methanedisulfonic acid ($R^1=R^2=H$, n=1); 1,2-ethanedisulfonic acid ($R^1=R^2=H$, n=2); 1,1-ethanedisulfonic acid ($R^1=CH_3$, $R^2=H$, n=1); 2,2-propanedisulfonic acid ($R^1=R^2=CH_3$, n=1) and 1,1-propanedisulfonic acid ($R^1=CH_2CH_3$, $R^2=H$, n=1).

In the present invention, commercially available sulfonic acid compounds may be used. Alternatively, a sulfonic acid compound obtained by a known method may be used. One example of a known method (disclosed in JP 2005-336155 A) is reacting water with an alkanedisulfonyl halide represented by General Formula (3),

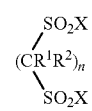 (3)

wherein $R^1$, $R^2$, and n are the same as those in General Formula (1) described above; and X is a halogen atom.

Examples of formaldehyde compounds usable in the present invention include paraformaldehyde, anhydrous formaldehyde obtained by heating paraformaldehyde, trioxane obtained by treating paraformaldehyde with acid, methylal and like acetalized formaldehydes. Among these, paraformaldehyde, anhydrous formaldehyde and trioxane are preferable. These formaldehyde compounds may be used singly or in combination.

The amount of formaldehyde compound is preferably 0.2 to 10 moles and more preferably 0.3 to 3 moles per mole of sulfonic acid compound. If the amount of formaldehyde compound is less than 0.2 moles, the reaction may not be completed; however, when it exceeds 10 moles, no effect corresponding to the amount used can be obtained and is thus uneconomical.

There is no limitation to the dehydrating agent used in the present invention and, for example, phosphorus pentoxide, phosphorus pentachloride, phosphorus oxychloride, thionyl chloride, acetyl chloride and acetic anhydride can be used. Among these, phosphorus pentoxide is preferable due to its high reactivity. These dehydrating agents may be used singly or in combination.

The amount of dehydrating agent is preferably 0.6 to 10 moles and more preferably 0.8 to 3 moles per mole of sulfonic acid compound. If the amount of the dehydrating agent is less than 0.6 moles, the reaction may not be completed; however, when it exceeds 10 moles, no effect corresponding to the amount used can be obtained and is thus uneconomical.

A solvent inactive to the reaction may be used in the present invention if necessary. Examples of such inactive solvents include toluene, xylene, monochlorobenzene, dichlorobenzene, trichlorobenzene, hexane, heptane, decane and like hydrocarbon-based solvents; diethyl ether, ethylene glycoldimethyl ether, diisopropyl ether, diphenyl ether, tetrahydrofuran, dioxane and like ether-based solvents; acetone, methyl ethyl ketone and like ketone-based solvents; dimethyl formamide, hexamethyl phosphorictriamide and like amide-based solvents; ethyl acetate and like acetate-based solvents; acetonitrile and like nitrile-based solvents; dimethyl sulfoxide, sulfolane and like sulfoxide/sulfone-based solvents.

The amount of solvent preferably does not exceed 1000 parts by weight per 100 parts by weight of the sulfonic acid compound.

The reaction temperature in the present invention is preferably 0 to 200° C., and more preferably 50 to 150° C. The reaction time depends on the reaction temperature but is preferably 0.1 to 10 hours.

The methylene disulfonate compound produced as described above is a compound represented by General Formula (2) below.

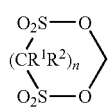
(2)

$R^1$, $R^2$, and n in General Formula (2) are the same as those in General Formula (1).

Examples of the methylene disulfonate compound represented by General Formula (2) include methylene methanedisulfonate ($R^1=R^2=H$, n=1), methylene 1,2-ethanedisulfonate ($R^1=R^2=H$, n=2), methylene 1,1-ethanedisulfonate ($R^1=CH_3$, $R^2=H$, n=1), methylene 2,2-propanedisulfonate ($R^1=R^2=CH_3$, n=1) and methylene 1,1-propanedisulfonate ($R^1=CH_2CH_3$, $R^2=H$, n=1).

The methylene disulfonate compound produced in the present invention can be isolated by several methods, such as subjecting a reaction solution to extraction using a solvent or the like, and then conducting crystallization after washing with water, etc; filtering a reaction solution and concentrating the filtrate; subjecting a reaction solution to sublimation refining; etc.

The methylene disulfonate compound represented by General Formula (2) can be obtained by reacting an acid anhydride of the sulfonic acid compound with the formaldehyde compound in the same manner as in the present invention. This reaction does not necessarily require a dehydrating agent. The acid anhydride can be obtained by, for example, reacting the corresponding sulfonic acid compound with phosphorus pentoxide or like dehydrating agent.

EFFECT OF THE INVENTION

The present invention allows a methylene disulfonate compound to be obtained in a simple manner at low cost.

BEST MODE FOR CARRYING OUT THE INVENTION

The present invention is explained in detail with reference to Examples below. However, the scope of the present invention is not limited to these Examples.

Example 1

In a 200 ml four-necked flask equipped with a stirrer, a condenser, and a thermometer, were placed 8.8 g (0.05 mole) of methanedisulfonic acid and 7.1 g (0.05 mole) of phosphorus pentoxide. To the mixture, 1.6 g (0.05 mole) of 92% paraformaldehyde was added while stirring at room temperature. After completion of the addition, the mixture was heated to 120° C. and stirred for one hour. The mixture was then cooled to room temperature and 100 g of methylene chloride was added thereto. After stirring for one hour, insoluble matter was filtered off. The resulting filtrate was concentrated to obtain crystals, and the resulting crystals were dried at 40° C. and 10 mmHg for 6 hours, giving 4.7 g of light brown crystals of methylene methanedisulfonate represented by General Formula (2) wherein $R^1$ and $R^2$ are hydrogen atoms, and n is 1. The yield of the resulting methylene methanedisulfonate was 50.0% relative to methanedisulfonic acid.

It was confirmed that the resulting light brown crystals were methylene methanedisulfonate by the following analysis results:
$^1$H-NMR (400 MHz, $CD_3CN$) δ (ppm): 5.33 (s, 2H), 6.00 (s, 2H).

Example 2

In a 200 ml four-necked flask equipped with a stirrer, a condenser, and a thermometer, were placed 9.5 g (0.05 mole) of 1,2-ethanedisulfonic acid and 8.5 g (0.06 mole) of phosphorus pentoxide. To the mixture, 2.0 g (0.06 mole) of 92% paraformaldehyde was added while stirring at room temperature. After completion of the addition, the mixture was heated to 120° C. and stirred for 10 hours. The mixture was then cooled to room temperature and 100 g of methylene chloride was added thereto. After stirring for one hour, insoluble matter was filtered off. The resulting filtrate was concentrated to obtain crystals, and the resulting crystals were dried at 40° C. and 10 mmHg for 6 hours, giving 7.0 g of light brown crystals of methylene 1,2-ethanedisulfonate represented by General Formula (2) wherein $R^1$ and $R^2$ are hydrogen atoms, and n is 2. The yield of the resulting methylene 1,2-ethanedisulfonate was 69.2% relative to 1,2-ethanedisulfonic acid.

It was confirmed that these light brown crystals were methylene 1,2-ethanedisulfonate by the following analysis results:

$^1$H-NMR (400 MHz, CD$_3$CN) δ (ppm): 3.83 (s, 4H), 5.63 (s, 2H).

The invention claimed is:

1. A process for producing a methylene disulfonate compound represented by General Formula (2) comprising:

reacting, in the presence of a dehydrating agent, a formaldehyde compound with a sulfonic acid compound represented by General Formula (1):

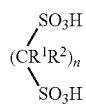

(1)

wherein $R^1$ and $R^2$ are independently a hydrogen atom or a C$_{1-4}$ alkyl group whose hydrogen atom may be substituted with halogen atom; n is an integer from 1 to 4; and when n is an integer from 2 to 4, n $R^1$s and n $R^2$s may be the same or different:

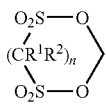

(2)

wherein, $R^1$, $R^2$, and n are the same as those described above for General Formula (1).

2. The process according to claim 1, wherein the formaldehyde compound is at least one member selected from the group consisting of paraformaldehyde, anhydrous formaldehyde and trioxane.

3. The process according to claim 1, wherein the dehydrating agent is phosphorus pentoxide.

* * * * *